United States Patent [19]
Bulusu

[11] Patent Number: 5,493,019
[45] Date of Patent: Feb. 20, 1996

[54] TETRAHYDROPYRAN DERIVATIVES

[75] Inventor: A. R. C. Murty Bulusu, Vienna, Austria

[73] Assignee: Sandoz Ltd., Basel, Switzerland

[21] Appl. No.: 249,911

[22] Filed: May 26, 1994

[30] Foreign Application Priority Data

| May 27, 1993 | [GB] | United Kingdom | 9310969 |
| May 27, 1993 | [GB] | United Kingdom | 9310975 |
| Jun. 18, 1993 | [GB] | United Kingdom | 9312590 |
| Jul. 1, 1993 | [GB] | United Kingdom | 9313553 |
| Sep. 23, 1993 | [GB] | United Kingdom | 9319617 |
| Sep. 23, 1993 | [GB] | United Kingdom | 9319618 |
| Dec. 21, 1993 | [GB] | United Kingdom | 9326045 |

[51] Int. Cl.$^6$ .................... C02D 491/16; A61K 31/395
[52] U.S. Cl. ........................................ 540/456; 540/452
[58] Field of Search ........................ 540/456, 452

[56] References Cited

FOREIGN PATENT DOCUMENTS

| 0478235 | 4/1992 | European Pat. Off. | 340/456 |
| 2249787 | 5/1992 | United Kingdom | 540/456 |
| WO9113889 | 9/1991 | WIPO | 540/456 |
| WO9213862 | 8/1992 | WIPO | 540/456 |

*Primary Examiner*—Robert T. Bond
*Attorney, Agent, or Firm*—Robert S. Honor; Melvyn M. Kassenoff; Thomas O. McGovern

[57] ABSTRACT

The invention concerns the compounds of formula I

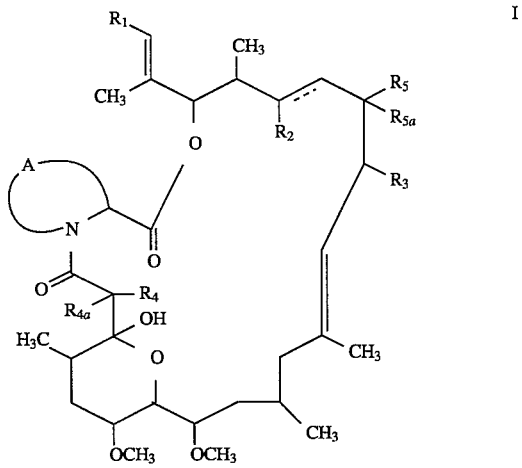

wherein the substituents have various significances, in free form and, where such forms exist, in salt form.

They can be prepared by various processes, e.g. by irradiation; oxidation; elimination; reduction; conversion by e.g. halogenation or acylation; deprotection of protected hydroxy groups; protection of free hydroxy groups; and separation of stereoisomeric mixtures into individual isomers.

They are useful as pharmaceuticals, especially as antiinflammatory, and as antiproliferative and antiinflammatory agents.

11 Claims, No Drawings

TETRAHYDROPYRAN DERIVATIVES

The present invention relates to the field of macrolides, especially tetrahydropyran derivatives. It concerns more particularly the compounds of the formula I

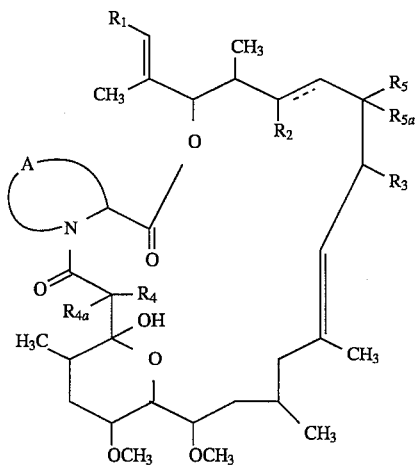

wherein
$R_1$ represents a group of formula

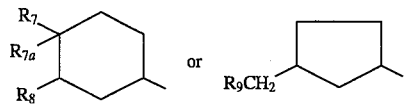

wherein
- either $R_7$ represents optionally protected hydroxy, acyloxy, halogen,—$OR_{10}$ wherein $R_{10}$ represents lower alkyl, optionally protected —$O(CH_2)_m OH$ wherein m is a number from 2 to 4, or —$OCONH_2$, and $R_{7a}$ represents hydrogen,
- or $R_7$ and $R_{7a}$ together represent oxo,
- $R_8$ represents hydroxy or methoxy, and
- $R_9$ represents hydroxy or acyloxy;
- $R_2$ represents hydrogen, acyloxy or optionally protected hydroxy and there is a single or a double bond between the two carbon atoms joined by a dotted line;
- $R_3$ represents methyl, ethyl, n-propyl or allyl;
- either $R_4$ represents hydrogen or hydroxy and $R_{4a}$ represents hydrogen,
- or R, and $R_{4a}$ together represent oxo;
- either $R_5$ represents hydroxy and $R_{5a}$ represents hydrogen,
- or $R_5$ and $R_{5a}$ together represent oxo; and
- A represents a group of formula —$CH(OR_6)$—$CH_2$—$(CH_2)_n$— or —$CH=CH$—$(CH_2)_n$—, whereby the $(CH_2)_n$— part thereof is linked to the carbon atom,
- $R_6$ represents lower alkyl and
- n represents the number 1 or 2;

in free form and, where such forms exist, in salt form, hereinafter briefly named "the compounds of the invention".

Optionally protected hydroxy as defined above under formula I for $R_2$ and $R_7$ should not be understood as including a group $R_2$ or $R_7$ which is otherwise specified, such as e.g. acyloxy or—$OCONH_2$.

It should further be understood that "protected hydroxy" or "protected —$O(CH_2)_m OH$" refers to pharmacologically active compounds having OH substituted with a group essentially conferring protection from degradation during chemical synthesis; the protecting group preferably is a conventional hydroxy protecting group such as tert-butoxycarbonyl or trialkylsilyl, especially tert-butyldimethylsilyl.

$R_1$ preferably represents a substituted cyclohexyl moiety as defined above. $R_2$ and $R_7$ preferably represent optionally protected hydroxy, especially hydroxy. $R_3$ preferably represents ethyl or allyl, especially ethyl. $R_4$ preferably represents together with $R_{4a}$ Oxo. $R_5$ preferably represents together with $R_{5a}$ oxo. $R_6$ preferably represents methyl or ethyl. $R_8$ preferably represents methoxy. $R_9$ preferably represents hydroxy. $R_{10}$ preferably represents methyl. m and n preferably represent the number 2. A preferably represents a group of formula —$CH=CH$—$(CH_2)_n$—.

Lower alkyl preferably is linear or branched alkyl with 1 to 4, especially 1 or 2, particularly 1 carbon atom(s). Halogen is fluorine, chlorine, bromine or iodine, preferably chlorine or bromine, especially chlorine. Hydroxy preferably is free hydroxy, i.e. unprotected. Acyloxy preferably is formyloxy, benzoyloxy or alkylcarbonyloxy of altogether 2 to 5 carbon atoms in the alkylcarbonyl part thereof.

Preferably there is a single bond between the two carbon atoms joined by a dotted line.

A preferred subgroup of compounds of formula I consists of the compounds of formula Ix

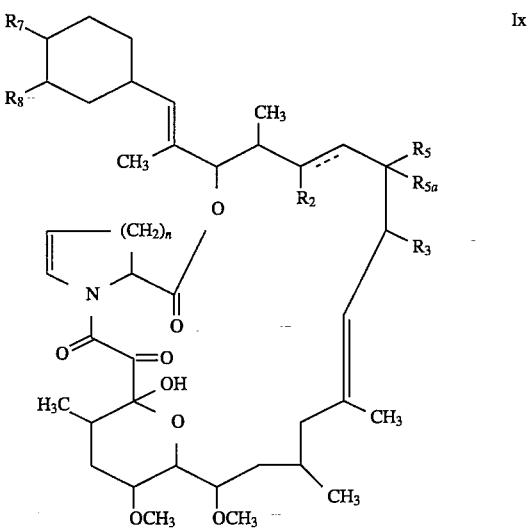

wherein the substituents are as defined above.

The compounds of the invention have a number of chiral centers and may thus exist in a variety of stereoisomers. The process variants of the invention result normally in a mixture of such isomers. Depending on the conditions and the type of reaction the process can be steered in such manner that a specific isomer preferably is produced. The invention provides all stereo- and optical isomers as well as racemic mixtures. The isomers may be resolved or separated by conventional techniques. The preferred stereochemistry at various chiral carbon atoms is shown in formula Is:

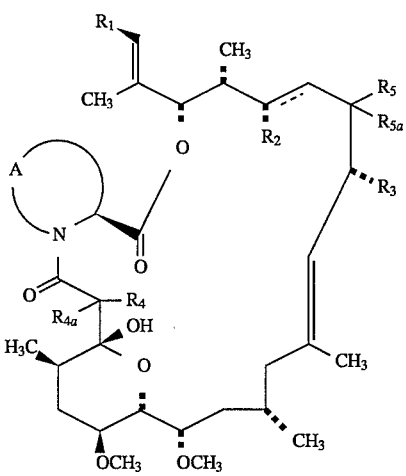

wherein the substituents are as defined above.

When $R_1$ is the substituted cyclohexyl group defined above wherein $R_7$ and $R_{7a}$ are other than oxo and $R_7$ is other than halogen, the preferred stereochemistry is shown by formula

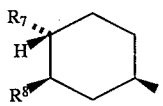

whereas when $R_7$ is halogen it preferably is in the β-configuration.

When $R_5$ is hydroxy it preferably is in the α-configuration.

The moiety $OR_6$ in group A preferably is in the β configuration. This additional chiral center is created in process variant a) for producing the compounds of formula Ia. The α and β isomers may be separated in conventional manner, e.g. chromatographically.

A further preferred subgroup of compounds of formula I consists of the compounds of formula Iss

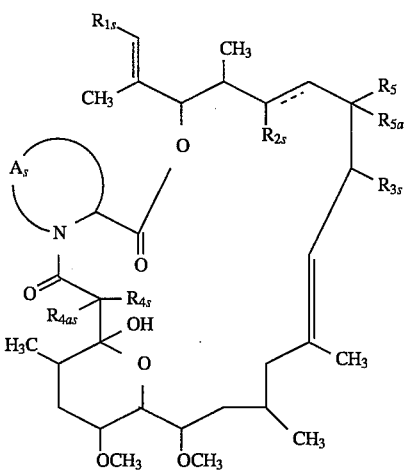

wherein $R_{1s}$ represents a group of formula

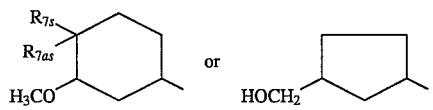

wherein either $R_{7s}$ represents a hydroxy or 2-hydroxyethoxy group optionally protected by tert-butyldimethylsilyl or represents isopropylcarbonyloxy or chlorine and $R_{7as}$ represents hydrogen, or $R_{7s}$ and $R_{7as}$ together represent oxo;

$R_{2s}$ represents hydrogen, isopropylcarbonyloxy or hydroxy and there is a single or a double bond between the two carbon atoms joined by a dotted line;

$R_{3s}$ represents ethyl or allyl;

$R_4$ and $R_{4a}$, and $R_5$ and $R_{5a}$ are as defined above; and $A_s$ represents a group of formula —CH(OR$_{6s}$)—CH$_2$—(CH$_2$)$_n$— or —CH=CH—(CH$_2$)$_n$—, whereby a CH$_2$-group is linked to the carbon atom, $R_{6s}$ represents methyl or ethyl and n is as defined above.

A further subgroup of compounds of formula I consists of the compounds of formula Ip$_1$

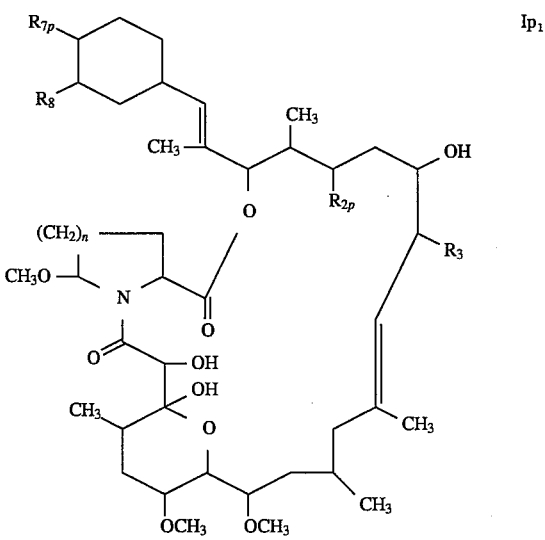

wherein $R_{2p}$ and $R_{7p}$ are the same or different and represent optionally protected hydroxy and the other substituents are as defined above.

A further subgroup of compounds of formula I consists of the compounds of formula Ip$_2$

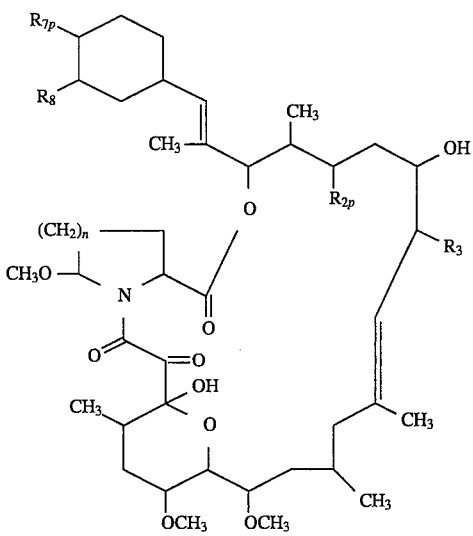

Ip₂ wherein the substituents are as defined above.

A further subgroup of compounds of formula I consists of the compounds of formula Ip₃

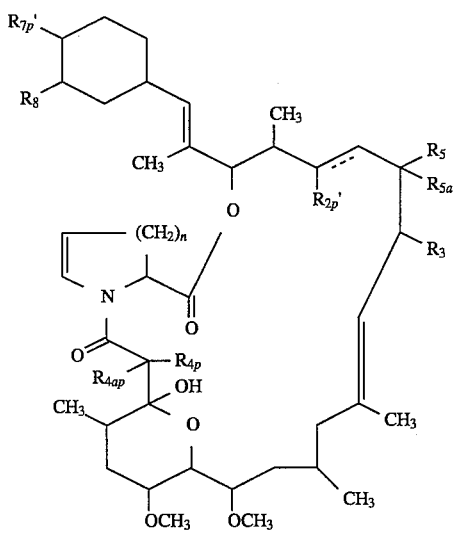

Ip₃ wherein
$R_{2p}'$ represents hydrogen or optionally protected hydroxy and there is a single or a double bond between the two carbon atoms joined by a dotted line;
either $R_{4p}$ represents hydroxy and $R_{4ap}$ represents hydrogen,
or $R_{4p}$ and $R_{4ap}$ together represent oxo;
$R_{7p}'$ represents halogen; and
the other substituents are as defined above.

A further subgroup of compounds of formula I consists of the compounds of formula Ip₄

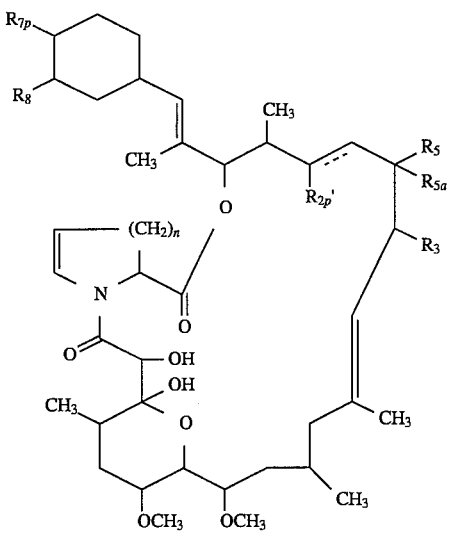

Ip₄ wherein the substituents are as defined above.

A further subgroup of compounds of formula I consists of the compounds of formula Ip₅

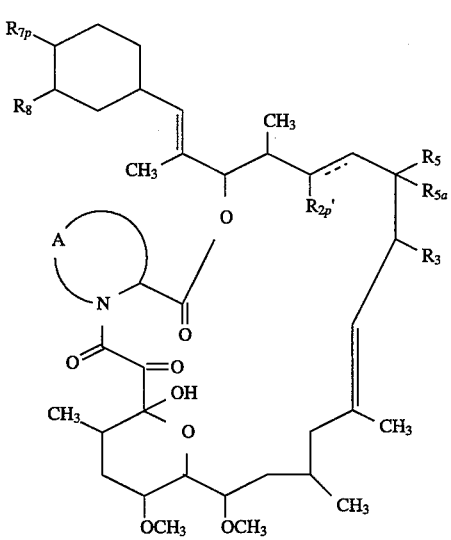

Ip₅ wherein the substituents are as defined above.

In a subgroup of compounds of formula Ip₅ A represents a group of formula —CH=CH—(CH₂)ₙ— as defined above. In a further subgroup A represents a group of formula —CH(OR₆)—CH₂—(CH₂)ₙ— as defined above, especially —CH(OCH₃)—CH₂—(CH₂)ₙ— wherein n is as defined above.

The compounds of the invention can be prepared by a process which comprises
a) for producing the compounds of formula Ia

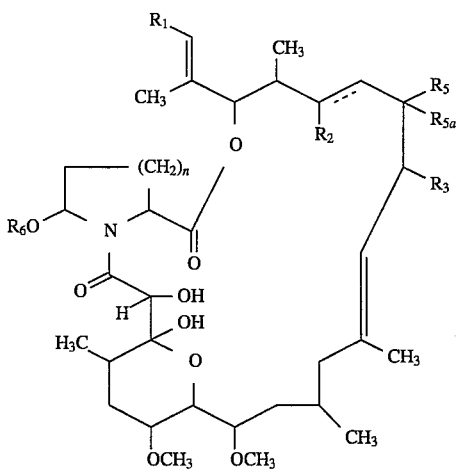

Ia

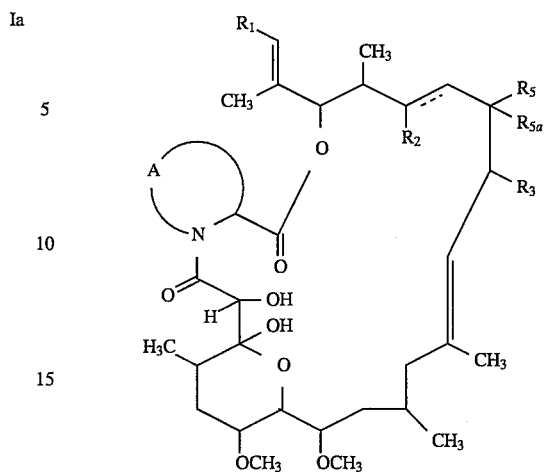

Ic wherein the substituents are as defined above, appropriately irradiating in the presence of $R_6OH$ corresponding compounds of formula II wherein the substituents are as defined above, or c) for producing the compounds of formula Id

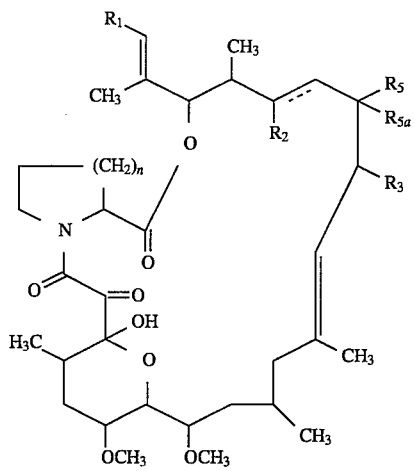

II

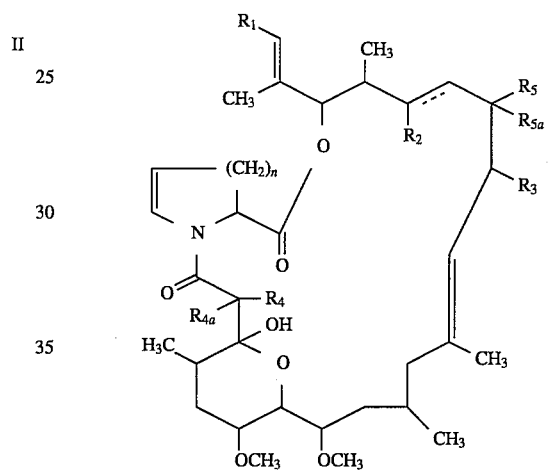

Id wherein the substituents are as defined above, or b) for producing the compounds of formula Ib wherein the substituents are as defined above, appropriately eliminating $R_6OH$ from corresponding compounds of formula Ie

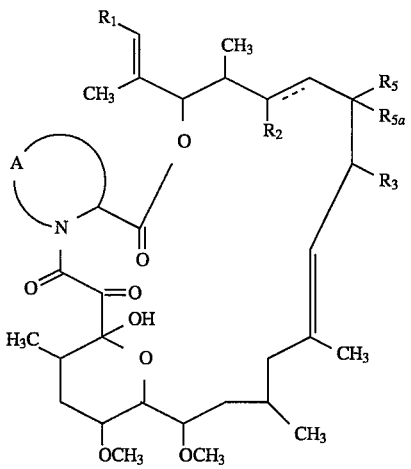

Ib

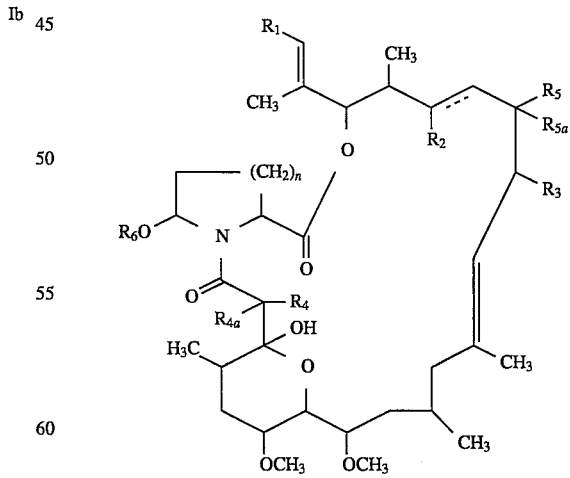

Ie wherein the substituents are as defined above, appropriately oxidizing corresponding compounds of formula Ic wherein the substituents are as defined above, or d) for producing the compounds of formula If

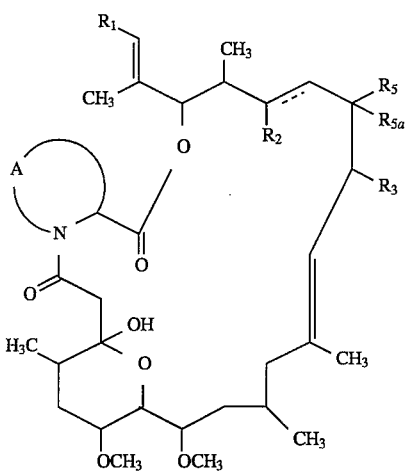

wherein the substituents are as defined above, appropriately reducing corresponding compounds of formula Ib; and
optionally converting reactive groups in resultant compounds of formula I having appropriate reactive groups, e.g.
 for producing compounds of formula I wherein $R_7$ represents halogen, by halogenating corresponding compounds of formula I wherein $R_7$ represents hydroxy, or
 for producing compounds of formula I wherein $R_2$, $R_7$ and/or $R_9$ represent acyloxy, by acylating corresponding compounds of formula I wherein $R_2$, $R_7$ and/or $R_9$ represent hydroxy;
optionally deprotecting one or more hydroxy group(s) in resultant compounds of formula I having protected hydroxy group(s), or protecting one or more hydroxy group(s) in resultant compounds of formula I having free hydroxy group(s);
optionally separating resultant stereoisomeric mixtures of compounds of formula I into individual isomers; and
recovering the compounds of formula I in free form or, where such forms exist, in salt form.

The process of the invention can be effected in conventional manner.

Process variant a) (irradiation) is a light-initiated intramolecular oxidation/reduction reaction. It may be carried out with UV and/or visible light, optionally under an inert gas atmosphere, e.g. with ultraviolet lamps emitting monochromatic or nonmonochromatic UV and/or visible light, e.g. at temperatures between about −78° and about 100° C., preferably between about 0° and about 30° C., preferably employing light filtered through pyrex or a long pass filter, e.g. an aqueous solution of NaBr and Pb(NO$_3$)$_2$ in an alcohol R$_6$OH or a mixture of an alcohol R$_6$OH with a saturated or unsaturated hydrocarbon, an ether, a ketone or an ester or a mixture of these solvents, whereby these solvents or components thereof may participate in the reaction or act, e.g. as sensitizer, and optionally in the presence of a further compound, which may participate in the reaction e.g. as a sensitizer or as an electron transfer assisting agent.

Process variant b) (oxidation) may be carried out in conventional manner, e.g. by reacting a compound of formula Ic with an oxidizing agent which selectively reacts with a hydroxy group adjacent to an oxo group, such as Cu(OAc)$_2$, in a solvent, e.g. in an alcohol such as methanol or a cyclic ether such as tetrahydrofuran or water or in a mixture of these solvents, under an O$_2$-atmosphere or in the presence of some other oxidizing agent, preferably at temperatures of between about 0° and about 90° C.

Process variant c) (elimination) may be carried out by reacting a compound of formula Ie e.g. with an acid such as HF, HCl or p-toluenesulfonic acid, preferably in a solvent such as acetonitrile, methanol, tetrahydrofuran, dichloromethane or dimethylformamide or water or a mixture of these solvents, preferably at temperatures between about −30° and about 100° C., or by reacting with a salt, such as NH$_4$Cl or NH$_4$Br, preferably in a solvent such as dimethylformamide, preferably at from about −30° to about 100° C., preferably under low pressure, whereby deprotection of a protected hydroxy group may be carried out in the same step or in a separate step.

Process variant d) (reduction) may be carried out e.g. by treating a compound of formula Ib with a reducing agent such as hydrogen sulfide, preferably in a solvent or a solvent mixture such as pyridine/dimethylformamide, preferably at temperatures of between about −70° and about 100° C.

Insofar as their preparation is not specifically described herein, e.g. in the Examples, the compounds used as starting materials are known or can be obtained in conventional manner from known compounds, e.g. starting from appropriate Streptomyces strains such as *Streptomyces tsukubaensis* No. 9993 described in e.g. Fujisawa EP 184162. Samples can be obtained from the Fermentation Research Institute, Tsukuba, Ibaraki 305, Japan under the provisions of the Budapest Treaty e.g. under deposit No. FERM BP-927. This strain has been redeposited on Apr. 27, 1989 with the Agricultural Research Culture Collection International Depository, Peoria, Ill. 61604, USA under the provisions of the Budapest Treaty under deposit No. NRRL 18488.

The compound of formula IIa

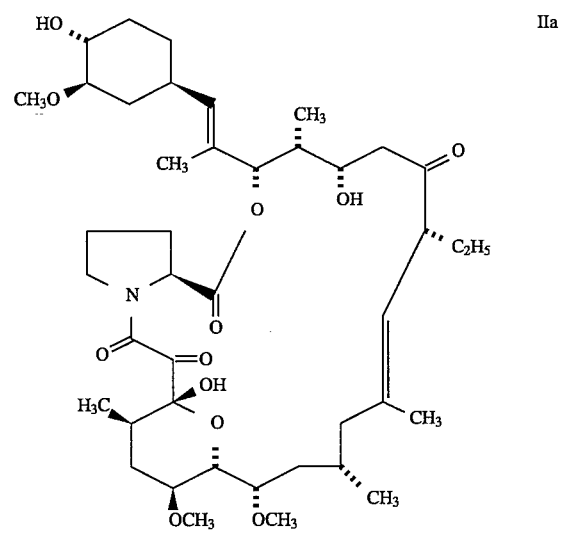

can be recovered in conventional manner from a microorganism capable of producing it, e.g. from a mutant strain (ATCC 55087) of *Streptomyces hygroscopicus* var. ascomycetus according to the procedure described! in EP 478235. ATCC 55087 has been redeposited on Apr. 13, 1994 with the American Type Culture Collection, Rockville, Md. 20852, USA under Deposit Number ATCC 55558, under the provisions of the Budapest Treaty.

The following Examples illustrate the invention. They are not limitative. All temperatures are in degrees Centigrade. In the NMR spectra all chemical shift values are in ppm; samples are measured in CDCl$_3$, unless indicated otherwise. The stereochemical configuration at the various carbon atoms is as for FK 506, except as indicated. All compounds are in free form. The following abbreviations are used:

AC=acetyl
cf=colourless foam db=double bond between the two carbon atoms joined by a dotted line
depr.=deprotection
iPr=isopropyl
m=mixture of stereoisomers with respect to the position indicated
m.p.=melting point
O=oxo
OtBDMS=tert-butyldimethylsilyloxy
sb=single bond between the two carbon atoms joined by a dotted line
tBDMS=tert-butyldimethylsilyl

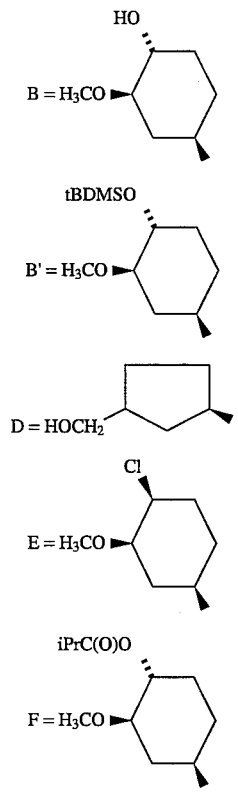

The conversion of reactive groups may be effected e.g. for halogenation by reacting with a halogenating agent such as dichloro triphenyl phosphorane in the presence of a base in an appropriate solvent, e.g. in toluene or tetrahydrofuran, at temperatures e.g. between about 0° C. and 70° C., and for acylation, by reaction e.g. in an inert solvent such as acetonitrile or dichloromethane, with an acyl chloride or an acyl anhydride in the presence of an acid binder such as 4-dimethylaminopyridine or with an acid in the presence of an acid binder such as 4-dimethylaminopyridine or with an acid in the presence of a carbodiimide such as dicyclohexylcarbodiimide.

The deprotection for the removal of e.g. tert-butyldimethylsilyl or tert-butoxycarbonyl may be effected e.g. by treatment with hydrofluoric or hydrochloric acid in a solvent such as acetonitrile, methanol, or a mixture of methanol and ether. Depending on the reaction conditions chosen (e.g. duration or temperature) the removal can be steered in such a manner that either all or only some protecting groups are eliminated. Partial deprotection is particularly indicated where a definite hydroxy group is to be reacted in a subsequent reaction.

For the protection of free hydroxy group(s), depending on the reaction conditions chosen the reaction can be steered in such a manner that either all or only some potentially reactive hydroxy groups are protected. Suitable protecting groups are conventional hydroxy protecting groups such as tert-butoxycarbonyl or trialkylsilyl, preferably tert-butyldimethylsilyl.

The separation of resultant stereoisomeric mixtures may be effected e.g. chromatographically.

The above process variants of the invention, e.g. a) and b) or a) and c), may be carried out also in a one pot reaction without isolating the intermediates.

A compound of the invention in free form may be converted into a salt form where such forms exist, e.g. an acid addition salt form, in conventional manner and vice-versa.

A compound of the invention may be isolated and purified from the reaction mixture in conventional manner.

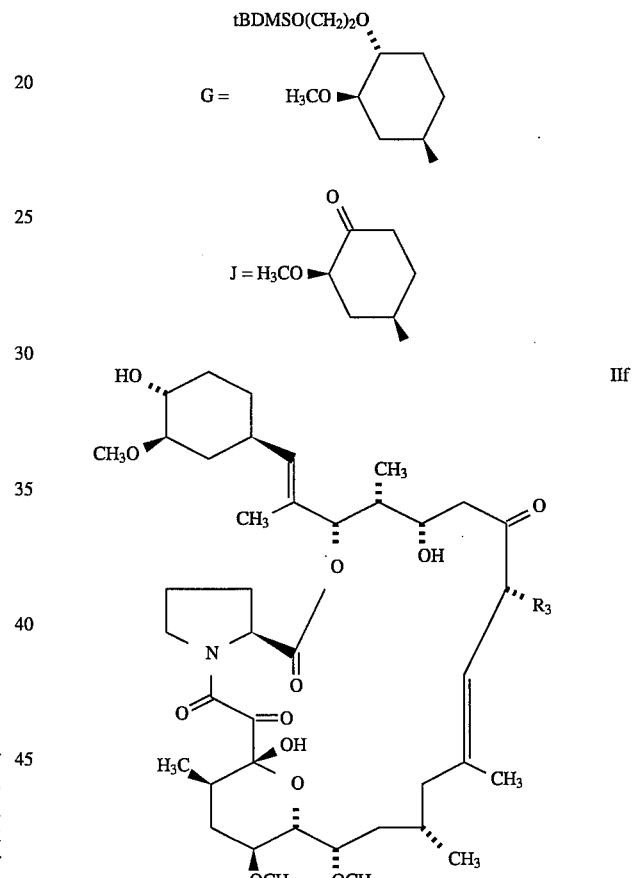

FK 506=compound of formula IIf wherein $R_3=CH_2CH=CH_2$
FR 520=compound of formula IIf wherein $R_3=C_2H_5$

EXAMPLE 1

Compound of Formula I $R_1=B$; $R_2=OH$; sb; $R_3=C_2H_5$; $R_4=OH(m)$;
$R_5s=OH(\alpha)$; $R_{4a}, R_{5a}=H$;
A=—CH(OR$_6$)—CH$_2$—(CH$_2$)$_2$— wherein
OR$_6$=OCH$_3(\beta)$ Process Variant: Deprotection 250 mg of the compound of Example 1a (see below), 10 ml of methanol and 0.15 ml of ether saturated with dry HCl is stirred in an ice-bath for 2 hours. The mixture is poured into aqueous bicarbonate solution and extracted with ethyl acetate. The organic phase is dried over $MgSO_4$ and the solvent is evaporated. Silicagel chromatography of the residue gives the title compound (cf).

EXAMPLE 1a

Compound of Formula I $R_1=B'$; other substituents=as for Example 1; sb

Process Variant: a)(Irradiation)

An argon degassed solution of 3.8 g of the compound of formula II [$R_1=B'$; $R_2=OH$; sb; $R_3=C_2H_5$; $R_5=OH(\alpha)$; $R_{5a}=H$; n=2] in 1200 ml of methanol is cooled in an ice-bath and irradiated in a well-type reactor for 10 hours using a Hanau TQ-150 lamp and employing a pyrex filter. Three such lots are combined and chromatographed by HPLC employing a polygosyl column using cyclohexane/isopropanol (9/1) to give the title compound (cf).

the residue partitioned between saturated aqueous bicarbonate and ethyl acetate, the organic phase is separated, dried ($MgSO_4$), filtered, the solvent is removed under vacuum and the residue is chromatographed over silicagel (pretreated with aqueous 2% w/w $NaHCO_3$ and dried in an oven) using ethyl acetate to give the title compound (foam). The foam is crystallised by dissolving in diethyl ether and adding n-pentane in small portions and scratching the walls with a spatula to initiate crystallization (m.p. 169°–172°).

EXAMPLE 9

Compound of Formula I $R_1=B$; $R_2=OH$; sb; $R_3=C_2H_5$; $R_4=OH(m)$; $R_{4a}=H$; $R_5+R_{5a}=O$; $A=-CH=CH-(CH_2)_2-$ Process Variant c)(Elimination)

A mixture of 50 mg of the compound of Example 2 and 100 mg of ammonium chloride in 100 ml of dimethylformamide is reacted for 1.5 hours in a rotatory evaporator

| Ex. No. | $R_1$ | $R_2$ | $R_3$ | $R_4$ | $R_{4a}$ | $R_5$ | $R_{5a}$ | A | sb or db | Configuration of $OR_6$ | $R_4$ | $R_5$ | Process variant | Characterization data |
|---|---|---|---|---|---|---|---|---|---|---|---|---|---|---|
| 2 | B | OH | $C_2H_5$ | OH | H | O | | $-CH(OCH_3)(CH_2)_3-$ | sb | β | m | — | a) | cf; NMR |
| 3 | B | OH | $C_2H_5$ | OH | H | O | | $-CH(OC_2H_5)(CH_2)_3-$ | sb | β | m | — | a) | cf; NMR |
| 4 | B | OH | $CH_2CH=CH_2$ | OH | H | O | | $-CH(OCH_3)(CH_2)_3-$ | sb | β | m | — | a) | cf; NMR |
| 5 | B | OH | $C_2H_5$ | OH | H | O | | $-CH(OCH_3)(CH_2)_2-$ | sb | β | m | — | a) | cf; NMR |
| 6 | B | OH | $C_2H_5$ | OH | H | O | | $-CH(OCH_3)(CH_2)_2-$ | sb | α | m | — | a) | cf; NMR |
| 7 | D | OH | $C_2H_5$ | OH | H | O | | $-CH(OCH_3)(CH_2)_3-$ | sb | β | m | — | a) | cf; NMR |

EXAMPLE 8

Compound of Formula I $R_1=B$; $R_2=OH$; sb; $R_3=C_2H_5$; $R_4+R_{4a}=R_5+R_{5a}=O$; $A=-CH=CH-(CH_2)_2-$ Process Variant b) (Oxidation)

A mixture of 5 g of the compound of Example 9 (see below), 1.9 g of $Cu(OAc)_2.H_2O$ and 500 ml of tetrahydrofuran is stirred at reflux temperature and under an $O_2$-atmosphere for 7 hours. The solvent is removed under vacuum, under vacuum at 78° so that the solvent slowly distills off. Remaining solvent is removed under high vacuum and the residue is partitioned between brine and ethyl acetate. The organic phase is separated, dried ($MgSO_4$), filtered, the solvent removed under vacuum and the residue subjected to flash chromatography over silicagel [pretreated with 2% w/w $NaHCO_3$ and dried in an oven] using ethyl acetate to give the title compound (foam). This foam is crystallized by dissolving in diethylether and adding n-pentane in small portions and scratching the walls with a spatula to initiate crystallization (m.p. 119°–123°).

| Ex. No. | $R_1$ | $R_2$ | $R_3$ | $R_4$ | $R_{4a}$ | $R_5$ | $R_{5a}$ | A | sb or db | Configuration of $OR_6$ | $R_4$ | $R_5$ | Process variant | Characterization data |
|---|---|---|---|---|---|---|---|---|---|---|---|---|---|---|
| 10 | B | H | $C_2H_5$ | | | O | | OH H | $-CH(OCH_3)(CH_2)_3-$ | sb | m | — | α/β | b) | cf; NMR |
| 11 | B | H | $C_2H_5$ | | | O | | OH H | $-CH(OCH_3)(CH_2)_3-$ | sb | α/β | — | α/β | b) | cf; NMR |
| 12 | B | OH | $C_2H_5$ | | | O | | OH H | $-CH(OCH_3)(CH_2)_3-$ | sb | β | — | a | b) | cf; NMR |
| 13 | B | OH | $C_2H_5$ | | | O | | O | $-CH(OC_2H_5)(CH_2)_3-$ | sb | β | — | — | b) | cf; NMR |
| 14 | B | OH | $CH_2CH=CH_2$ | | | O | | O | $-CH(OCH_3)(CH_2)_3-$ | sb | β | — | — | b) | cf; NMR |
| 15 | B | OH | $C_2H_5$ | | | O | | O | $-CH(OCH_3)(CH_2)_2-$ | sb | α | — | — | b) | cf; NMR |
| 16 | B | OH | $C_2H_5$ | | | O | | O | $-CO(OCH_3)(CH_2)_2$ | sb | β | — | — | b) | cf; NMR |
| 17 | B | OH | $C_2H_5$ | | | O | | OH H | $-CH(OCH_3)(CH_2)_2-$ | sb | α | — | α | b) | cf; NMR |
| 18 | B | OH | $C_2H_5$ | | | O | | O | $-CH(OCH_3)(CH_2)_3-$ | sb | β | — | — | b) | cf; NMR |
| 19 | B | OH | $C_2H_5$ | OH | H | OH | H | $-CH=CH-(CH_2)_2-$ | sb | — | m | α | c) | cf; NMR |
| 20 | B | OH | $CH_2CH=CH_2$ | OH | H | O | | $-CH=CH-(CH_2)_2-$ | sb | — | m | — | c) | cf; NMR |
| 21 | B | OH | $C_2H_5$ | OH | H | O | | $-CH=CH-CH_2-$ | sb | — | m | — | c) | cf; NMR |
| 22 | D | OH | $C_2H_5$ | OH | H | O | | $-CH=CH-(CH_2)_2-$ | sb | — | m | — | c) | cf; NMR |
| 23 | E | OH | $C_2H_5$ | | | O | | O | $-CH=CH-(CH_2)_2-$ | sb | — | — | — | b) c) | cf; NMR |
| 24 | B | OH | $CH_2CH=CH_2$ | | | O | | O | $-CH=CH-(CH_2)_2-$ | sb | — | — | — | b) c) | cf; NMR |
| 25 | B | OH | $C_2H_5$ | | | O | | O | $-CH=CH-CH_2-$ | sb | — | — | — | b) c) | cf; NMR |
| 26 | B | OH | $C_2H_5$ | | | O | | OH H | $-CH=CH-(CH_2)_2-$ | sb | — | — | α | b) c) | cf; NMR |

-continued

| Ex. No. | $R_1$ | $R_2$ | $R_3$ | $R_4$ | $R_{4a}$ | $R_5$ | $R_{5a}$ | A | sb or db | Configuration of $OR_6$ | $R_4$ | $R_5$ | Process variant | Characterization data |
|---|---|---|---|---|---|---|---|---|---|---|---|---|---|---|
| 27 | B | OCOiPr | $C_2H_5$ | | O | | O | —CH=CH—$(CH_2)_2$— | sb | — | — | — | b) c) | cf; NMR |
| 28 | F | OCOiPr | $C_2H_5$ | | O | | O | —CH=CH—$(CH_2)_2$— | sb | — | — | — | b) C) | cf; NMR |
| 29 | B | H | $C_2H_5$ | | O | | O | —CH=CH—$(CH_2)_2$— | db | — | — | — | b) c) | cf; NMR |
| 30 | B | H | $C_2H_5$ | | O | | O | —CH=CH—$(CH_2)_2$— | sb | — | — | — | b) c) | cf; NMR |
| 31 | D | H | $C_2H_5$ | | O | | O | —CH($OCH_3$)$(CH_2)_3$— | sb | β | — | — | b) | cf; NMR |
| 32 | D | H | $C_2H_5$ | | O | | O | —CH=CH—$(CH_2)_2$— | sb | — | — | — | b) c) | cf; NMR |
| 32a | G | OH | $C_2H_5$ | | O | | O | —CH=CH—$(CH_2)_2$— | sb | — | — | — | b) c) | cf; NMR |
| 32b | J | OH | $C_2H_5$ | | O | | O | —CH=CH—$(CH_2)_2$— | db | — | — | — | b) c) | cf; NMR |
| 32c | B | OH | $C_2H_5$ | | O | | O | —CH=CH—$(CH_2)_2$— | db | — | — | — | b) c) | cf; NMR |

EXAMPLE 33

Compound of Formula I $R_1$=B; $R_2$=OH; sb; $R_3$=$C_2H_5$; $R_4$=$R_{4a}$=H; $R_5$+$R_{5a}$=O; A=—CH=CH—$(CH_2)_2$—

Process Variant d) (Reduction)

$H_2S$ gas is passed for 10 minutes through a mixture of 200 mg of the compound of Example 8, 0.3 ml of pyridine and 4.8 ml of dimethylformamide. The reaction mixture is stirred at room temperature for 24 hours. $H_2S$ gas is passed through the mixture again for 10 minutes. The mixture is stirred at room temperature for an additional period of two days. The mixture is diluted with toluene and the solvents are removed under high vacuum. The residue is partitioned between ethyl acetate and saturated aqueous sodium bicarbonate solution. The organic phase is separated, washed with brine, dried over $MgSO_4$, and the solvent removed under vacuum. The residue is flash chromatographed over silicagel (pretreated with 2% aqueous bicarbonate) using ethyl acetate to give the title compound (foam).

| Ex. | Spectra: |
|---|---|
| | $^1$H-NMR - Spectra |
| 1 | 5.83(t, J=2.6Hz); 5.29(br, d, J=4.1 Hz); 4.32(d, J=8.5Hz); 3.70(dd, J=1.2 and 9.5Hz); 3.13(s). |
| 10 | (major component): 5.63(br, d); 3.84(dd). |
| 11 | (major component): 5.69(br, t); 4.61(dd, J=2.0, 5.5); 3.21(s). |
| 17 | 4.96(t, J=2.8Hz); 4.19(dd, J=3.7 and 8.6Hz); 3.92(m); 3.63(d, J=9.6Hz); 3.33(s). |
| 18 | (ca. 2:1 mixture of isomers) major isomer: 5.69(t, J=2.7Hz); 5.21(d, J=9.0Hz); 5.10(d, J=1.6Hz); 4.92(d, J=10.1Hz); 4.46(dd, J=5.3 and 1.8Hz). |
| 27 | (ca. 1:1 mixture of isomers): 7.11(d, J=8.4); 6.89(d, J=8.4); 3.03–2.96(m); 2.54–2.46(m); 1.16–1.12(m). |
| 28 | (ca. 1:1 mixture of isomers): 7.10(d, J=8.6); 6.89(d, J=8.4); 4.71–4.64(m); 3.90(dd, J=9.5, 3.0); 2.57–2.48(m); 1.1 8–1.12(m). |
| 30 | 6.86(d, J=8.6 Hz); 7.13(d, J=8.5Hz). |
| 32a | (ca. 0.5:0.7 mixture of isomers): 7.12(d, J=8.5); 6.82(d, J=8.6); 3.79–3.59 (several multiplets); 3.38(s); 3.30(s); 0.90(broad singlet). |
| 32b | (mixture of isomers): 7.05(d, J=8.5); 6.43(d, J=8.4); 5.67(s); 5.62(s); 3.90–3.85(m). |
| 32c | (mixture of isomers): 7.09(d, J=8.7); 6.52(d, J=8.5); 5.69(s); 5.64(s); 3.07–3.0(m). |
| | $^{13}$C-NMR-Spectra |
| 1a | 173.8, 170.6, 136.7, 130.4, 129.3, 125.5, 97.3, 84.3, 80.1. |
| 2 | (main component): 214.0, 173.3, 170.7, 139.7, 131.1, 129.7, 123.9, 97.0, 80.5, 75.2, 52.1. |
| 3 | (main component): 214.0, 173.1, 170.3, 139.7, 132.6, 130.1, 123.9, 96.9, 84.2, 78.2, 76.9, 75.3, 74.9, 73.52, 73.46, 72.5, 71.1, 63.7, 52.2. |
| 4 | (main component): 213.2, 173.3, 170.7, 139.9, 135.7, 131.2, 129.7, 123.3, 116.5, 97.0, 84.2, 80.5, 77.7, 75.2, 52.1. |
| 5 | (main component): 213.1, 173.2, 169.2, 140.2, 131.9, 130.0, 122.8, 99.6, 88.3, |

| Ex. | Spectra: |
|---|---|
|  | 84.2, 78.5, 77.0, 74.1, 73.5, 71.6, 71.2, 69.3, 59.7, 54.2. |
| 6 | (main component): 213.0, 173.0, 170.6, 140.0, 132.3, 130.3, 123.6, 99.2, 88.4, 84.1, 79.0, 77.3, 74.2, 73.5, 72.2, 71.2, 69.9, 59.8, 55.8, 54.0. |
| 7 | (major isomer): 214.1, 173.4, 170.7, 139.7, 123.9, 97.0, 67.3. |
| 8 | (main component): 213.9, 190.8, 167.7, 162.9, 139.5, 131.9, 129.8, 123.9, 123.2, 109.7, 98.9, 53.0. |
| 9 | (main component): 212.9, 171.2, 168.8, 140.3, 132.4, 130.3, 125.4, 123.1, 106.7, 99.5. |
| 12 | 195.2, 169.5, 167.5, 136.5, 130.6, 129.0, 125.3, 96.5, 84.3, 79.5, 78.2, 53.8, 49.4 |
| 13 | (main component): 213.6, 195.7, 169.0, 167.3, 138.8, 132.2, 130.3, 123.5, 97.0, 84.2, 63.8, 54.5. |
| 14 | (main component): 212.9, 195.4, 169.1, 167.3, 139.0, 135.5, 131.2, 129.9, 123.1, 6.7, 96.9, 84.3, 79.4. |
| 15 | 214.5, 188.1, 168.6, 164.4, 140.2, 132.3, 129.5, 122.8, 98.7, 88.8, 84.2, 78.0, 76.1, 73.5, 71.7, 69.2, 59.0, 57.0, 56.6, 56.3, 55.6, 55.3 |
| 16 | 213.6, 188.0, 168.1, 163.9, 139.9, 131.6, 130.0, 123.1, 99.1, 88.6, 84.2, 78.4, 76.1, 73.6, 71.4, 69.1, 59.0, 55.0. |
| 19 | 169.8, 169.0, 138.0, 131.7, 128.3, 127.7, 123.4, 109.0, 98.4, 55.4 |
| 20 | (main component): 211.9, 171.2, 168.9, 140.4, 135.5, 132.4, 130.4, 125.3, 122.4, 116.5, 106.7, 99.5, 84.1, 78.7, 69.0. |
| 21 | 213.4, 170.0, 169.0, 140.3, 132.1, 130.6, 130.4, 122.9, 109.3, 100.0, 84.1, 78.9, 74.1, 73.5, 71.4, 70.5, 69.4, 59.0. |
| 22 | (major isomer): 212.7, 171.5, 168.9, 140.1, 132.1, 131.7, 125.4, 123.1, 106.6, 99.7, 67.1 |
| 23 | (ca. 2:3 mixture of isomers): 214.2, 213.3, 168.2, 167.6, 162.9, 139.6, 138.9, 132.1, 131.8, 129.8, 129.2, 123.9, 123.23, 123.16, 121.9, 112.1, 109.8, 98.9, 97.5 |
| 24 | (main component): 213.0, 194.5 or 190.9, 167.7, 162.9, 139.6, 135.4, 131.9, 129.8, 123.9, 122.6, 116.7, 109.7, 98.9, 84.2. |
| 25 | 213.7, 187.0, 167.7, 159.0, 140.3, 132.0, 130.4, 129.4, 122.8, 113.2, 99.2, 84.2, 79.0, 76.5, 73.58, 73.55, 71.5, 69.1, 59.0, 57.7, 56.5, 56.2, 55.4 |
| 26 | (main component): 195.7, 168.0, 162.8, 135.4, 131.4, 128.3, 127.9, 123.0, 109.5, 99.6, 52.6 |
| 29 | (ca. 45:40 mixture of isomers): 201.4, 199.4, 194.9, 188.8, 168.4, 167.5, 163.3, 163.1, 148.1, 145.3, 139.1, 138.2, 133.9, 131.4, 129.9, 129.6, 129.5, 127.7, 124.0, 123.7, 123.5, 121.8, 110.9, 110.2, 99.0, 98.1 |
| 31 | 213.8, 195.4, 169.2, 167.4, 138.7, 123.8, 96.9, 83.4, 79.4, 78.3, 74.7, 73.6, 72.6, 71.5, 67.4 |
| 32 | 213.9, 190.8, 167.7, ~163, 139.5, 123.9, 123.2, 109.7, ~99, 67.3 |
| 33 | 214.8, 170.9, 168.1, 140.9, 132.6, 129.2, 123.7, 122.3, 107.3, 98.5, 84.2, 77.4, 76.9, 74.2, 73.6, 70.9, 69.4, 37.4 |

The compounds of formula I in free form and, where salt forms exist, in pharmaceutically acceptable salt form, hereinafter briefly named the "agents of the invention", possess pharmacological activity. They are thus useful as pharmaceuticals. In particular they possess antiinflammatory, and immunosuppressant and antiproliferative activity.

The antiinflammatory activity may e.g. be determined in the following test methods:

1. Inhibition of mast cell degranulation in vitro (the test method is as described in e.g. EP 569337):

The agents of the invention inhibit in this test degranulation of mast cells ($IC_{50}$) at concentrations as low as 50 nM.

2. Oxazolone-induced allergic contact dermatitis (mouse) in vivo (the test method is as described in e.g. F. M. Dietrich and R. Hess, *Int. Arch. Allergy* 38 (1970), 246–259):

The agents of the invention elicit in this test an activity (inhibition of inflammatory swelling) of up to 50% upon a single topical application as a 0.01% solution. Hydrocortisone (1.2%) is inactive under these conditions in this model.

3. DNFB-induced allergic contact dermatitis (swine) in vivo (the test method is as described in e.g. EP 315 978):

Two topical applications of a 0.13% formulation of the agents of the invention result in inhibition of the inflammatory reaction by up to 50%.

The immunsuppressant and antiproliferative activity may e.g. be determined in the following test methods:

4. Inhibition of proliferative response of lymphocytes to allogen stimulation in the mixed lymphocyte reaction (MLR) in vitro [the test method is as described in e.g. T. Moo, "The MLR in the Mouse", *Immunological Methods*, L. Lefkovits and B. Pernis, Eds, Academic Press, N.Y. (1979), 227–239]:

The agents of the invention suppress in this test lymphocytes proliferation ($IC_{50}$) at concentrations as low as 1 nM.

Pharmaceutical compositions e.g. for topical application comprising an agent of the invention in association with at least one pharmaceutically acceptable carrier or diluent may be manufactured in conventional manner by mixing with a pharmaceutically acceptable carrier or diluent. Unit dosage forms contain, for example, from about 2.5 mg to about 50 mg of active substance.

Topical administration is e.g. to the skin. A further form of topical administration is to the eye, for the treatment of immune-mediated conditions of the eye, such as: autoimmune diseases, e.g. uveitis, keratoplasty and chronic keratitis; allergic conditions, e.g. vernal conjunctivitis; inflammatory conditions and corneal transplants, by the topical administration to the eye surface of an agent of the invention in a pharmaceutically acceptable ophthalmic vehicle.

The ophthalmic vehicle is such that the agent is maintained in contact with the ocular surface for a sufficient time period to allow the agent to penetrate the corneal and internal regions of the eye, e.g. the anterior chamber, posterior chamber, vitreous body, aqueous humor, vitreous humor, cornea, iris/ciliary, lens, choroid/retina and sclera. The pharmaceutically acceptable ophthalmic vehicle may be e.g. an ointment, vegetable oil, or an encapsulating material.

Another form of topical treatment is the application of the agents of the invention to bronchial and alveolar epithelia via inhalation of e.g. aerosol or powder in e.g. asthmatic patients.

The agents of the invention inhibit antigen-induced inflammatory cell infiltration into the airways following topical administration to the airways via the pulmonary route. They are thus useful in the treatment of airways or lung diseases, such as asthma. This activity may be demonstrated in standard test methods, e.g. by measurement of the influence on allergen-induced pulmonary eosinophilia (in vivo), as described in e.g. EP 577544.

The agents of the invention are accordingly useful in the treatment of diseases or conditions responsive to or requiring topical therapy of the airways or lung, in particular inflammatory or obstructive airways disease. They are especially useful in the treatment of diseases or conditions of the airways or lung associated with or characterized by inflammatory cell infiltration or other inflammatory events accompanied by inflammatory cell, e.g. eosinophil and/or neutrophil, accumulation, most especially in the treatment of asthma. They are also useful in the treatment of bronchitis or for the treatment of chronic or acute 5. Inhibition of proliferation of human keratinocytes in vitro (the test method is described in e.g. EP 539 326):

The agents of the invention are active in this test at concentrations as low as 7 μM, resulting in an inhibition of about 50%.

6. Macrophilin-12 binding assay in vitro [the test method is as described in K. Baumann et al., *Tetrahedron Letters* 34 (1993), 2295–2298]:

The agents of the invention bind to macrophilin with an affinity ($IC_{50}$) comparable to that of rapamycin and of FK 506.

7. IL-2 reporter gene assay in vitro [the test method is as described in G. Baumann et al., *Transpl. Proc.* 24/Suppl. 2(1993), 43–48]:

The agents of the invention elicit in this test an $IC_{50}$ at a concentration as low as 0.2 nM.

The compound of Example 8 ("5,6-dehydro-ascomycin"), which may also be designated by the full chemical name 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0 $^{4,9}$]octacosa-5,18-diene-2,3,10,16-tetraone [1R,5Z,9S, 12S-[1E(1 R,3R, 4R)], 13R,14S,17R,18E, 21S,23S,24R,25S,27R], is the preferred agent for the above indications. It has for example been determined that in the above test 3. this compound in the form of a 0.13% preparation has better activity than a corresponding 0.13% preparation of dexamethasone. It is, therefore, indicated that for the above uses this compound may be administered to larger mammals, for example humans, by similar modes of administration at similar or lower dosages than conventionally employed with dexamethasone.

The agents of the invention, particularly the compound of Example 8, show less skin atrophy after topical application as compared to potent topical corticosteroids and also less systemic side effects as compared to FK 506, as shown e.g. by evaluating toxicity in rats upon subcutaneous administration.

The agents of the invention are therefore useful as anti-inflammatory agents and as immunosuppressant and antiproliferative agents for topical and systemic use in the prevention and treatment of inflammatory and hyperproliferative conditions and of conditions requiring immunosuppression such as:

a) the treatment of inflammatory and hyperproliferative skin diseases, such as psoriasis, atopical dermatitis, contact dermatitis and further eczematous dermatoses, seborrhoeic dermatitis, Lichen planus, Pemphigus, bullous Pemphigoid, Epidermolysis bullosa, vasculitides, erythemas, cutaneous eosinophilias, Lupus erythematosus and acne;

b) the prevention and treatment of allergic diseases such as extrinsic asthma, rhinitis, conjunctivitis, atopic eczema, urticaria/angioedema, food/drug allergy and anaphylaxis;

c) the prevention and treatment of resistance in situations of organ or tissue transplantation, e.g. of heart, kidney, liver, bone marrow and skin, graft-versus-host diseases, such as following bone marrow grafts, and auto-immune deseases such as rheumatoid arthritis, systemic Lupus erythematosus, Hashimoto's thyroidis, multiple sclerosis, Myasthenia gravis, diabetes type I and uveitis, skin manifestations of immunologically-mediated disorders; and d) Alopecia areata.

The agents may be administered systemically or topically. For use in the above indications the appropriate dosage will, of course, vary depending upon, for example, the particular agent employed, the host, the mode of administration and the nature and severity of the condition being treated. However, in general, beneficial results are indicated to be obtained systemically at daily dosages of from about 0.15 mg/kg to about 1.5 mg/kg animal body weight. An indicated daily dosage in the larger mammal is in the range of from about 10 mg to about 100 mg, conveniently administered, for example, in divided doses up to four times a day or in retard form. For topical use satisfactory results are obtained with local administration at a concentration of active substance of about 0.1% to about 3% several times daily, e.g. 3 times daily. Examples of indicated galenical forms are lotions, gels, creams, sprays and solutions.

The agents of the invention may be administered by any conventional route, in particular enterally, e.g. orally, e.g. in the form of tablets or capsules, or topically, e.g. in the form of lotions, gels, creams, sprays, ophtalmic or nasal solutions or aerosols for local treatment of skin and mucosal membranes, e.g. the eye, respiratory tract, vagina, oral and nasal cavity. airways obstruction associated therewith, of pneumoconiosis and of eosinophil-related disorders of the airways.

For the above purposes, the agents of the invention may be employed in any dosage form appropriate for topical administration to the desired site e.g. via the pulmonary route by inhalation from an appropriate dispenser device, e.g. in any suitable finely dispersed or finely dispersible form capable of administration into the airways or lungs, for example in finely divided dry particulate form or in dispersion or solution in any appropriate (i.e. pulmonarily administrable) solid or liquid carrier medium. For administration in dry particulate form, the agents of the invention may, for example, be employed as such, i.e. in micronised form without any additive materials, in dilution with other appropriate finely divided inert solid carrier or diluent, in coated particulate form or in any other appropriate form as known in the art for the pulmonary administration of finely divided solids.

Pulmonary administration may be effected using any appropriate system as known in the art for delivering drug sub:stance in dry or liquid form by inhalation, e.g. an atomiser, nebulizer, dry-powder inhaler or like device. Preferably a metered delivery device, i.e. capable of delivering a pre-determined amount of agent of the invention at each actuation, will be employed. Such devices are known in the art.

Pharmaceutically acceptable diluents or carriers acceptable for topical administration pulmonarily include e.g. dry powder preparations of the active ingredient (i.e. agent of the invention) in substantially pure form, for example as employed in the art for delivery from a dry powder inhalation device. Means or devices enabling or facilitating topical administration include, in particular, inhalation devices as well as containers and the like from which the active ingredient may be delivered in a form capable of topical application. Preferred embodiments will be such as permit topical administration within the airways or lungs, e.g. by inhalation.

Dosages of agent of the invention employed for treating diseases or conditions of the airways or lungs, e.g. for use in treating inflammatory or obstructive airways disease, for example asthma, e.g. by inhalation, are of the order of from 0.1 mg to 10 mg per day, e.g. from about 0.5 mg to about 5 mg, preferably from about 1 mg to about 3 mg per day. Dosages will appropriately be administered from a metered delivery system in a series of from 1 to 5 puffs at each administration, with administration performed once to four times daily. Dosages at each administration will thus conveniently be of the order of from about 0.0025 mg to about 10 mg, more suitably from about 0.125 mg to about 5 mg, e.g. administered with a metered delivery device, e.g. capable of delivering from about 0.25 mg to about 3 mg agent per actuation.

Whilst the antiinflammatory and the immunosuppressant and antiproliferative activity is the main activity of the agents of the invention, they also possess some degree of activity in increasing sensitivity to, or in increasing the efficacy of, chemotherapeutic drug therapy. This activity may e.g. be determined according to the test methods described in EP 360760.

The agents of the invention are therefore also useful in reversing chemotherapeutic drug resistance of varying types, e.g. acquired or innate, or in increasing sensitivity to administered drug therapy, e.g. as a means of reducing regular chemotherapeutic dosage levels, for example in the case of anti-neoplastic or cytostatic drug therapy, as a means of decreasing overall drug toxicity and, more especially, as a means of reversing or reducing resistance, including both inherent and acquired resistance, to chemotherapy.

The invention thus also concerns the use of an agent of the invention as a pharmaceutical, particularly as an antiinflammatory, and as an immunosuppressant and antiproliferative agent. It further provides a pharmaceutical composition comprising an agent of the invention in association with at least one pharmaceutically acceptable carrier or diluent. It further provides a method of treatment of inflammatory and of hyperproliferative conditions and conditions requiring immunosuppression which comprises administering a therapeutically effective amount of an agent of the invention to a patient in need of such treatment.

I claim:

1. A compound of formula I wherein $R_1$ represents a group of formula wherein either $R_7$ represents optionally protected hydroxy, acyloxy, halogen, —$OR_{10}$ wherein $OR_{10}$ represents lower alkoxy, optionally protected —$O(CH_2)_m OH$ wherein m is a number from 2 to 4, or —$OCONH_2$, and $R_{7a}$ represents hydrogen, or $R_7$ and $R_{7a}$ together represent oxo, $R_8$ represents hydroxy or methoxy, and $R_9$ represents hydroxy or acyloxy;

$R_2$ represents hydrogen, acyloxy or optionally protected hydroxy and there is a single or a double bond between the two carbon atoms joined by a dotted line;

$R_3$ represents methyl, ethyl, n-propyl or allyl;

either $R_4$ represents hydrogen or hydroxy and $R_{4a}$ represents hydrogen, or $R_4$ and $R_{4a}$ together represent oxo;

either $R_5$ represents hydroxy and $R_{5a}$ represents hydrogen, or $R_5$ and $R_{5a}$ together represent oxo; and A represents a group of formula —$CH(OR_6)$—$CH_2$—$(CH_2)_n$— or —$CH=CH$—$(CH_2)_n$—, whereby the $(CH_2)_n$— part thereof is linked to the carbon atom, $R_6$ represents lower alkyl and n represents the number 1 or 2;

in free form or in pharmaceutically salt form.

2. A compound according to claim 1 of formula Ix wherein the substituents are as defined in claim 1.

3. A compound according to claim 1 of formula Is

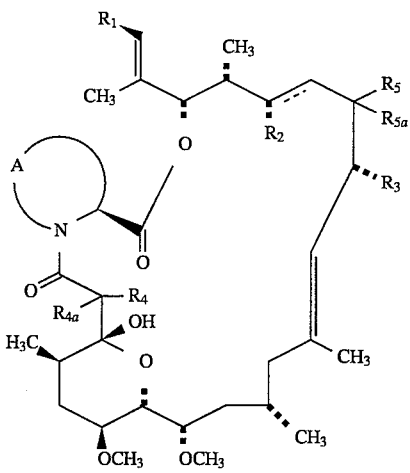

wherein the substituents are as defined in claim 1.

4. A compound according to claim 1 of formula Iss

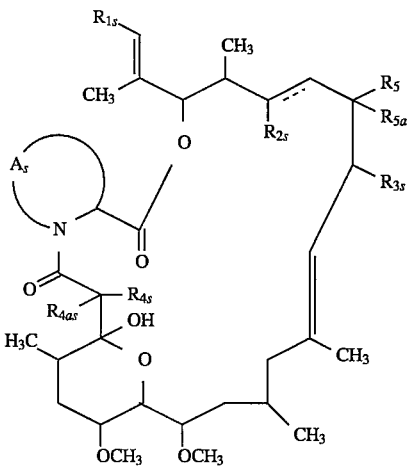

wherein $R_{1s}$ represents a group of formula

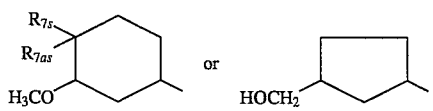

wherein either $R_{7s}$ represents a hydroxy or 2-hydroxyethoxy group optionally protected by tert-butyldimethylsilyl or represents isopropylcarbonyloxy or chlorine and $R_{7as}$ represents hydrogen, or $R_{7s}$ and $R_{7as}$ together represent oxo;

$R_{2s}$ represents hydrogen, isopropylcarbonyloxy or hydroxy and there is a single or a double bond between: the two carbon atoms joined by a dotted line;

$R_{3s}$ represents ethyl or allyl;

$R_4$ and $R_{4a}$, and $R_5$ and $R_{5a}$, are as defined in claim 1, $A_s$ represents a group of formula —CH(OR$_6$)—CH$_2$—(CH$_2$)$_n$— or —CH=CH—(CH$_2$)$_n$—, whereby a CH$_2$-group is linked to the carbon atom, $R_{6s}$ represents methyl or ethyl and n is as defined in claim 1.

5. A compound according to claim 1 of formula Ip$_1$

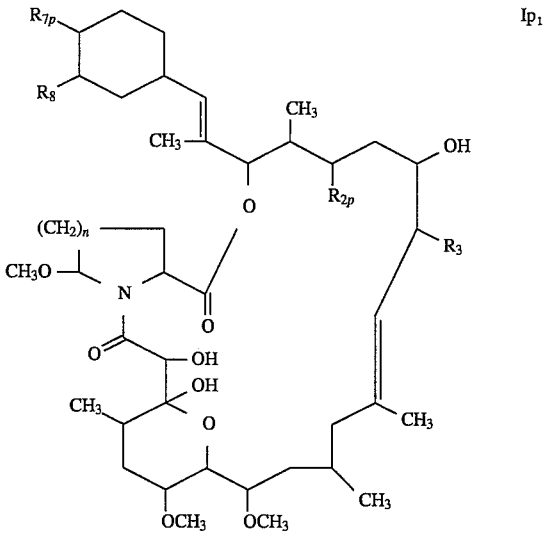

wherein $R_{2p}$ and $R_{7p}$ are the same or different and represent optionally protected hydroxy and the other substituents are as defined in claim 1.

6. A compound according to claim 1 of formula Ip$_2$

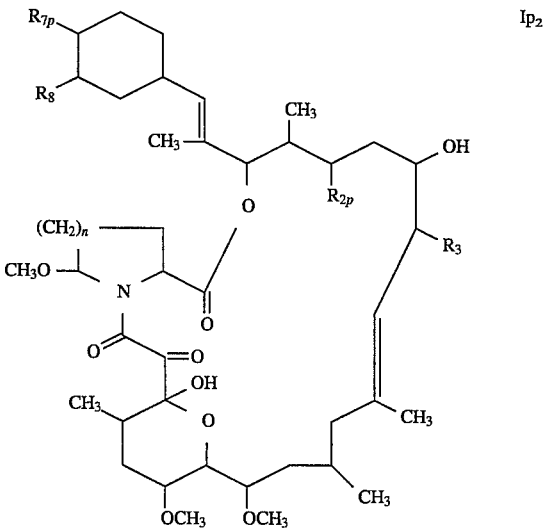

wherein $R_{2p}$ and $R_{7p}$ are the same or different and represent optionally substituted hydroxy.

7. A compound according to claim I of formula Ip$_3$

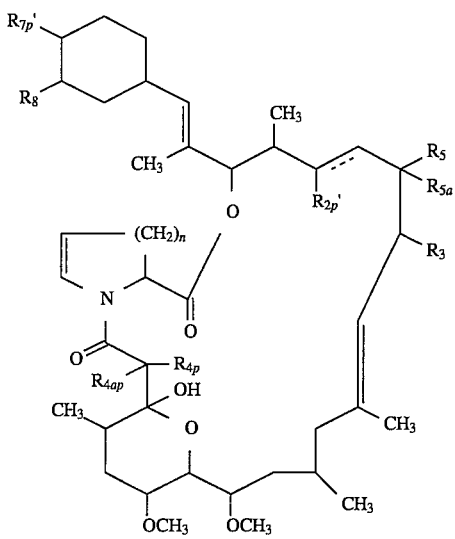

wherein
  $R_{2p}'$ represents hydrogen or optionally protected hydroxy and there is a single or a double bond between the two carbon atoms joined by a dotted line;
  either $R_{4p}$ represents hydroxy and $R_{4ap}$ represents hydrogen,
  or $R_{4p}$ and $R_{4ap}$ together represent oxo;
  $R_{7p}'$ represents halogen;
and the other substituents are as defined in claim 1 or in this claim.

8. A compound according to claim 1 of formula $I_{p4}$

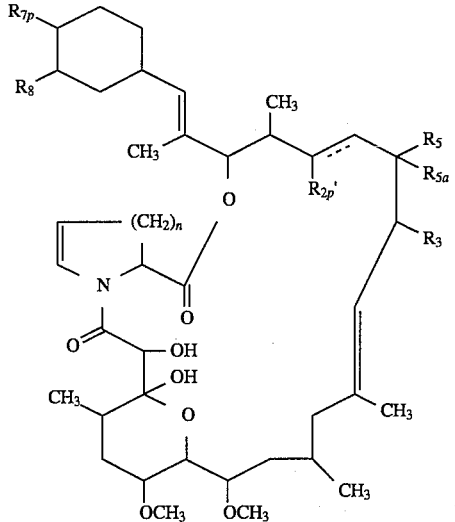

wherein $R_{2p}'$ represents hydrogen or optionally protected hydroxy and there is a Single or a double bond between the two carbon atoms joined by a dotted line; and $R_{7p}$ represent optionally substituted hydroxy.

9. A compound according to claim 1 of formula $I_{p5}$

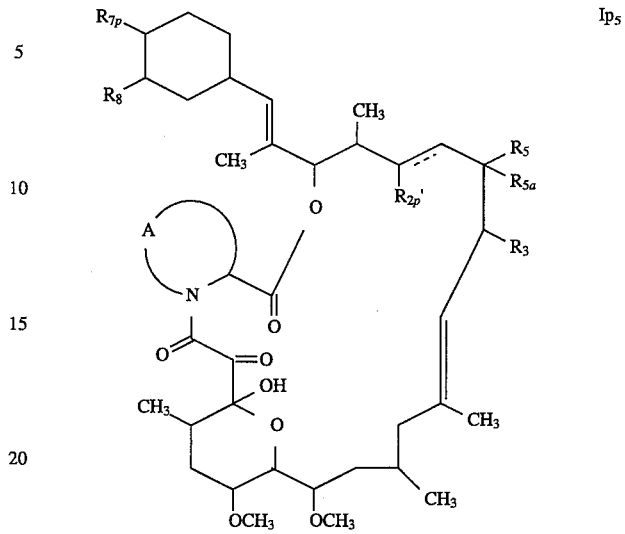

wherein $R_{2p}'$ represents hydrogen or optionally protected hydroxy and there is a single or a double bond between the two carbon atoms joined by a dotted line; and $R_{7p}$ represent optionally substituted hydroxy.

10. The compound according to claim 1 of formula I wherein
  $R_1$ represents a group of formula B

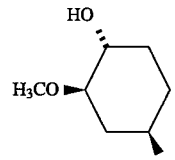

$R_2$ represents hydroxy and there is a single bond between the two carbon atoms joined by a dotted line,
  $R_3$ represents ethyl,
  $R_4$ represents hydroxy in the α- or β-configuration,
  $R_5$ represents hydroxy in the α-configuration,
  $R_{4a}$ and $R_{5a}$ represent hydrogen, and
  A is a group —CH(OR$_6$)—CH$_2$—(CH$_2$)$_2$— wherein OR$_6$ represents methoxy in the β-configuration,
and the stereochemical configuration at the various other asymmetrically substituted carbon atoms is as for FK 506.

11. The compound of formula I which is 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0.$^{4,9}$]-octacosa-5,18-diene-2,3,10,16-tetraone [1R,5Z,9S,12S-[1E(1R,3R,4R)], 13R,14S, 17R,18E,21S,23S,24R,25S,27R].

* * * * *